United States Patent [19]
Walinsky et al.

[11] Patent Number: 5,486,192
[45] Date of Patent: Jan. 23, 1996

[54] CYCLIC CORONARY ANGIOPLASTY SYSTEM

[76] Inventors: Paul Walinsky, 8910 Carlisle Rd., Wyndmoor, Pa. 19118; William H. Meise, P.O. Box 344, Penns Park, Pa. 18943

[21] Appl. No.: 253,720

[22] Filed: Jun. 3, 1994

[51] Int. Cl.⁶ .................................................. A61M 29/00
[52] U.S. Cl. ............................................. 606/194; 604/96
[58] Field of Search .................................. 606/192, 194; 604/96–104; 600/18

[56] References Cited

U.S. PATENT DOCUMENTS

| | | | |
|---|---|---|---|
| 5,158,529 | 10/1992 | Kanai | 600/18 |
| 5,169,379 | 12/1992 | Freed et al. | 600/18 |
| 5,217,429 | 6/1993 | Kanai | 600/18 |
| 5,300,017 | 4/1994 | Isoyama et al. | 600/18 |
| 5,365,933 | 11/1994 | Elghazzawi | 128/697 |

OTHER PUBLICATIONS

Angioplasty, Jang, David G., M.D., (McGraw–Hill Book Co. 1986), pp. vii–ix.

*Primary Examiner*—John D. Yasko
*Assistant Examiner*—Adam J. Cermak

[57] ABSTRACT

A conventional balloon catheter is used in conjunction with an inflation control system which senses the heartbeat electrically or by way of arterial pressure, and which controls the balloon inflation condition in synchronism therewith, thereby deflating the balloon during periods, such as diastole (heart muscle relaxation), to allow blood to flow past the deflated balloon, and inflating the balloon during systolic (heart muscle contraction) periods, so that the plaque may be compressed, or the walls of the artery or other vas may be expanded by the inflated balloon. Since blood can pass the location of the balloon during each heartbeat, nutrient blood flow continues during the angioplasty procedure, so the procedure may be continued for a longer time than during conventional treatment. Since the blood flow is "time-division multiplexed" using a conventional angioplasty catheter, the catheter may be smaller andor more flexible than a conventional perfusion catheter, allowing its use in smaller arteries, and at lower catheter cost. The heart sensor may include a plurality of electrodes such as are ordinarily used for electrocardiograms (EKGs) or an arterial pressure sensor, connected to a control circuit which responds to a distinctive portion of the electrical signal therefrom. In a particular embodiment of the invention, action potentials may be obtained from a location adjacent the balloon.

3 Claims, 2 Drawing Sheets

CYCLIC CORONARY ANGIOPLASTY SYSTEM

BACKGROUND OF THE INVENTION

This invention relates to the medical procedure of angioplasty, and more particularly to angioplasty performed in a cyclic manner which may be synchronous with the rhythm of the heartbeat.

Several hundred thousand people die in the United States each year from acute myocardial infarction, and many more suffer from chronic heart problems. A major contributing factor in both acute and chronic heart problems is a reduction ill nutrient blood flow to the muscles of the heart resulting from a reduction of blood flow through the coronary blood vessels. The reduction in flow may be caused by deposits of atherosclerotic plaque on the walls of the blood vessel, which causes a narrowing of the lumen or channel of the blood vessel. When the lumen is sufficiently narrowed, the rate of flow of blood may be so diminished that spontaneous formation of a thrombus or clot occurs by a variety of physiological mechanisms. As is known, once a blood clot has started to develop, it extends within minutes into the surrounding blood, in part because the proteolytic action of thrombin acts on prothrombin normally present, tending to split this into additional thrombin which causes additional clotting. Thus, the presence of atherosclerotic plaque not only reduces the blood flow to the heart muscle which it nourishes, but is a major predisposing factor in coronary thrombosis.

Among the treatments available for the conditions resulting from plaque formations are pharmacological means such as the use of drugs, for example nitroglycerin, for dilating the coronary blood vessels to improve flow. Surgical treatment may be indicated. One of the surgical techniques commonly used is the coronary bypass, in which a substitute blood vessel shunts or bypasses blood around the blockage. The bypass operation is effective but is expensive and subject to substantial risks.

A technique which has recently received a good deal of attention is transluminal laser catheter angioplasty. This treatment involves introduction into the coronary artery of a fiber optic cable, the proximal end of which is connected to a laser energy source. The distal end of the fiber optic cable is directed toward the plaque. The laser is pulsed, and the resulting high energy light pulse vaporizes a portion of the plaque. Many problems remain unsolved in laser catheter angioplasty, such as matching the characteristic of lasers and fiber optic cables to the frequency absorption characteristics of various types of plaque, and the by-products of the destruction of the plaque.

Percutaneous transluminal balloon catheter angioplasty is an alternative form of treatment. In general, an angioplasty procedure is performed by obtaining access to the interior of a coronary artery partially obstructed by plaque, and advancing a deflated balloon to the location of the stenosis. The balloon is inflated by applying fluid pressure through an inflation/deflation ("inflation") lumen of the catheter, to thereby apply balloon pressure tending to expand the lumen of the coronary artery. When the stenotic portion of the lumen of the blood vessel or coronary artery has about the same diameter as adjacent portions which are free from plaque, the procedure may be terminated, the balloon deflated and the catheter removed. The lumen remains expanded after removal of the catheter. It has been observed, as mentioned in the article entitled "Perfusion During Coronary Angioplasty," by Rossen, published at pages 103–106 in the June 1989 issue of Cardio, that increased time with the balloon inflated is associated with an improved result, which is to say that the longer the stenotic region remains dilated by the balloon, the more likely it is to stay open. The art relating to angioplasty includes many advances, such as the microwave-aided angioplasty described in U.S. Pat. No. 4,643,186, issued Feb. 17, 1987 in the name of Rosen et al., which heats the affected region to aid in softening the plaque to allow it to expand more readily under balloon pressure.

Those portions of the heart muscle supplied with blood flow through the artery are at least partially deprived of blood flow when the catheter with deflated balloon is being positioned in the stenotic region, and may be completely deprived of blood flow when the balloon is inflated. This in turn has a tendency to decrease heart pumping efficiency, and the blood pressure tends to drop. Chest pains result in some patients. Either of these, indications may undesirably require early termination of the procedure, which may produce a less than optimal result.

Dilatation catheters are available, as described in the above-mentioned Rossen article, in which perfusion or blood flow past the occluding catheter and balloon is provided by fenestrations or apertures into the distal lumen of the catheter on both sides of the balloon. Such perfusion catheters tend to be somewhat larger in diameter and stiffer than conventional catheters having the same inflated balloon diameter, and are therefore more difficult to position. Also, their larger diameter excludes them from use in the small arteries into which conventional balloon catheters may fit. Another type of perfusion catheter, described in U.S. Pat. No. 5,108,370, issued Apr. 28, 1992, in the name of Walinsky, includes an annular or toroidal balloon defining a central perfusion aperture, through which blood can flow while the balloon is inflated, thereby allowing nutrient blood flow to tissues located downstream of the balloon.

SUMMARY OF THE INVENTION

A conventional balloon catheter is introduced into a coronary artery, and is used in conjunction with an inflation control system which operates cyclically to automatically inflate and deflate the balloon. In one embodiment of the invention, the apparatus senses the heartbeat, and controls the balloon inflation condition in synchronism therewith, thereby inflating the balloon during periods, such as systole, when the heart muscle contraction limits coronary artery inflow, so that the plaque may be compressed, or the walls of the artery may be expanded by the inflated balloon, and deflating the balloon during diastolic periods in which the heart muscle relaxes, allowing coronary artery fellow. Since blood can pass the location of the deflated balloon during the diastole of each heartbeat or set of heartbeats, nutrient blood flow continues during the angioplasty procedure, so the procedure may be continued for a longer time than during conventional treatment. Since the blood flow is "time-division multiplexed" using a conventional angioplasty catheter, the catheter may be smaller andor more flexible than a conventional perfusion catheter, allowing its use in smaller arteries, and at lower catheter cost. The heart sensor may include a plurality of electrodes of the type which are ordinarily used for electrocardiograms (EKGs), or associated with the catheter, and connected to a control circuit which responds to a distinctive portion of the electrical signal therefrom. The heart sensor may instead be a blood pressure sensor associated with the catheter. In a particular embodiment of the invention, the action potentials are

DESCRIPTION OF THE INVENTION

Figure 1:
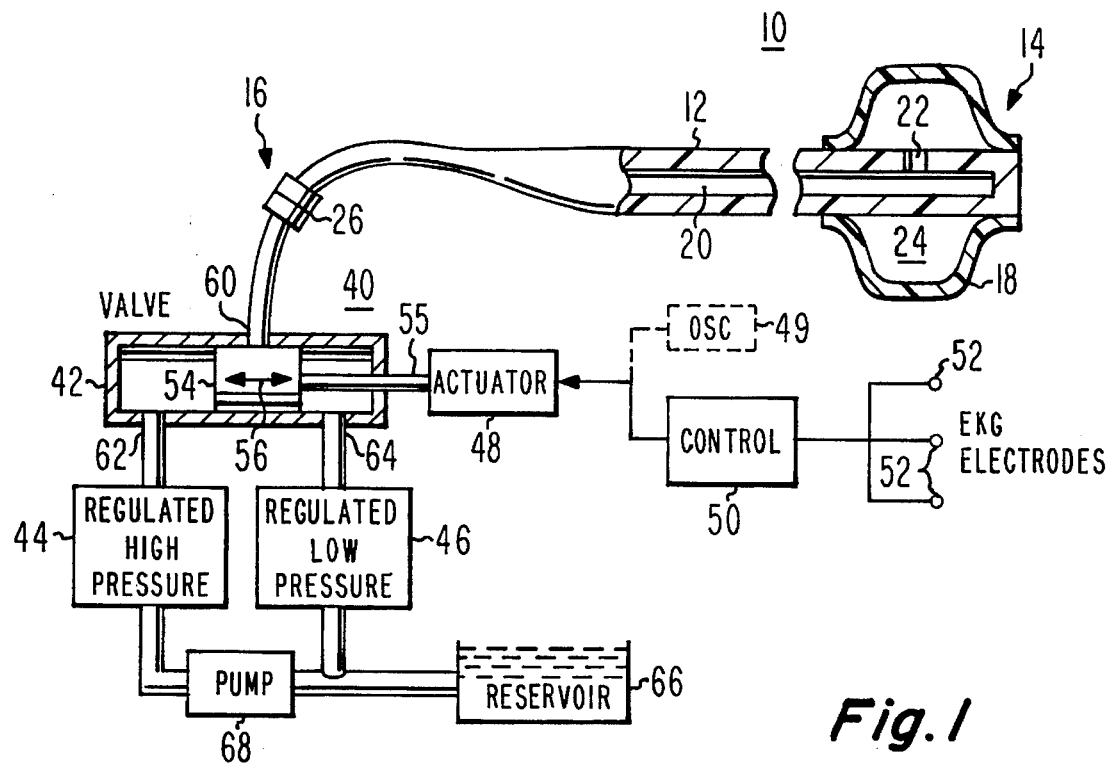
FIG. 1 is a simplified block diagram of a balloon angioplasty apparatus according to the invention.

FIG. 1 is a simplified block diagram of an apparatus according to the invention. In FIG. 1, a vascular catheter designated generally as 10, seen partially in section, includes a body 12 defining a distal end 14 and a proximal end 16. Body 12 of catheter 10 supports a balloon or membrane bag 18 near its distal end. The balloon is illustrated in its inflated condition. The distal end of the catheter in its deflated condition is dimensioned to fit within the desired coronary artery. Inflation fluid is supplied to balloon 18 by way of an inflation lumen 20 extending longitudinally through body 12, which opens into the interior chamber 24 of balloon 18 at an inflation aperture 22. At the proximal end of catheter 10, a connector 26 couples the inflation aperture to a controllable inflation apparatus designated generally as 40.

Controllable inflation apparatus 40 includes a two-way inflation fluid valve 42, a high-pressure reservoir 44, a low-pressure reservoir 46, a control valve actuator 48, and a controller 50 which operates on action potentials or voltages originating at the heart of the patient, received from electrodes, represented as 52, or alternatively which acts in response to arterial blood pressure sensors.

Valve 42 is seen in cross-section, and includes an elastomeric or other type of sealing plunger 54 movable laterally by a rod 55, in the directions of arrows 56, under control of actuator 48. The illustrated position of plunger 54 is a central position. Valve 42 has three ports. The first port of valve 42 is a catheter port 60 connected to connector 26, where it can be connected to the inflation lumen of catheter 10. A second port of valve 42 is a "high" pressure port 62, which is connected to a source of relatively high pressure balloon inflation pressure, illustrated as a reservoir 44. The third port of valve 42 is "low" pressure port 64, which is connected to a source of relatively low balloon deflation pressure, illustrated as a reservoir 46. The fluid may be a liquid, such as saline solution, possibly mixed with a contrast fluid, or it may be a gas, for which carbon dioxide is preferred because of its compatibility with body tissues, and its rapid reabsorption by the body. For completeness, a fluid reservoir 66 and a pump 68 are illustrated, which represent those well-known portions of the apparatus which are required to produce the desired, preferably regulated, fluid pressures. Desirably, the set-points of the pressure regulators (not illustrated) for the inflation and deflation pressures are independently settable, to thereby provide maximum flexibility in optimizing operation of the apparatus to fit the conditions of the particular patient.

Figure 2A:
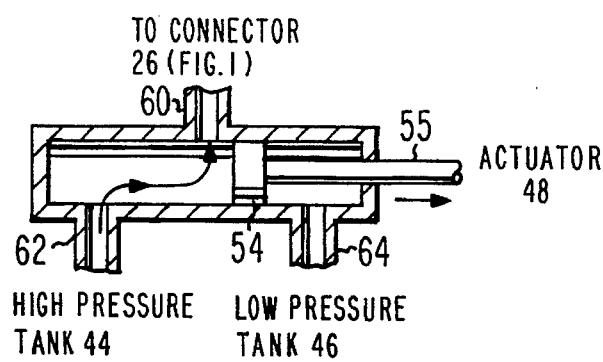
FIGS. 2a and 2b are cross-sectional representations of a fluid control valve of FIG. 1, with two different positions of its plunger.
Figure 2B:
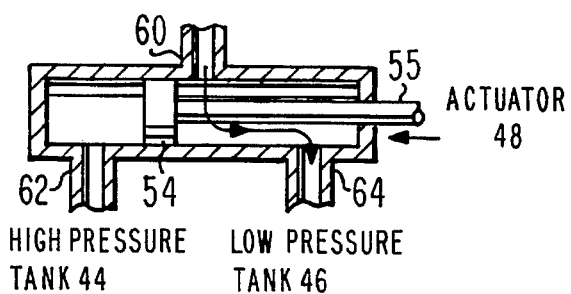

FIG. 2a is a cross-section of valve 42 of FIG. 1 with plunger 54 at a position to the right of port 60, whereby a continuous path for the flow of balloon inflation fluid at a relatively high pressure is formed between port 62 and port 60. FIG. 2b is a similar cross-section with plunger 54 at a position to the left of port 60, whereby a path for the flow of fluid is formed from port 60 to port 64.

Instead of an elastomeric plunger 54 as described in conjunction with FIG. 1, a washer or other arrangement may be used for sealing at the plunger to prevent inflation fluid from leaking from the higher pressure side of the valve to the lower pressure side. In this regard, the terms "higher" and "lower" pressure are meant as relative to each other, and are selected in view of the type of catheter, the amount of pressure necessary to dilate the blood vessels being treated, and the like; those skilled in the art will know what pressures are appropriate in a given context. Angioplasty balloons, which are required to expand against resistant body tissues, may require substantial pressures, which may be on the order of two to twenty atmospheres.

While a deflation "pressure" has been described, those skilled in the art will recognize that a negative pressure or vacuum may also be used in the context of the invention.

Actuator 48 of FIG. 1 may be a simple solenoid actuator, or it may include a position sensor coupled to the controller, described below, for providing positional feedback. Actuator 48 may be connected to an oscillator 49, illustrated as a dashed block 49, for automatic cyclic control at the oscillator rate. A preferred embodiment, described below, synchronizes the operation of actuator 48 with the heartbeat. In the preferred embodiment of the invention, actuator 48 of FIG. 1 is controlled by a control signal from controller 50 rather than by oscillator 49.

Figure 3:
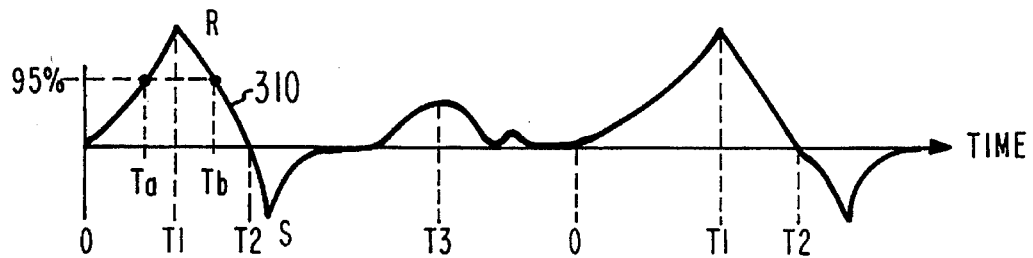
FIG. 3 is a simplified representation of at least one cycle of action potentials or heart voltages which may be sensed by external electrodes.

FIG. 3 is a very simplified representation or plot of voltages which may be sensed by electrodes attached to the body of a patient, which originate from heart action. In FIG. 3, plot 310 includes peak portions and valley portions. The art of obtaining such "electrocardiogram" (EKG) voltages is very advanced, and systems for processing the voltages by analog methods, and particularly by digital methods, are well known in the art. For purposes of the present invention, all that is necessary is to roughly synchronize the inflation and deflation of the balloon with the heartbeat, so that the balloon is inflated when the heart is "squeezing" to propel blood through the circulatory system, and deflated when the heart is at reduced pressure, thereby allowing fellow of blood into the coronary arteries. In principle, only two electrodes are necessary to sense the voltages, but more may be used. The plot of FIG. 3 might alternatively be viewed as being a plot generated by an arterial blood pressure sensor, and the signal may be processed much as described above.

It should be noted that the inflation of the balloon during systole is counterintuitive, in that systole is the time during which the heart muscle squeezes, to thereby increase arterial blood pressure, to cause blood flow through the arteries of the body. It would appear on the surface that the balloon should be deflated during this interval, so that blood could flow through the coronary arteries when the blood pressure peaks. However, the coronary arteries are unlike the remaining arteries of the body, in that the heart muscle, when it squeezes to increase the arterial blood pressure, also squeezes the coronary arteries, thereby reducing blood flow therethrough. The blood flow in the coronary arteries is at a maximum during diastole, when the heart muscle relaxes, because the coronary arteries are no longer squeezed, and are allowed to expand. The expansion of the coronary arteries during diastole causes an inflow of oxygenated blood, even though the arterial blood pressure is relatively low.

Figure 4:
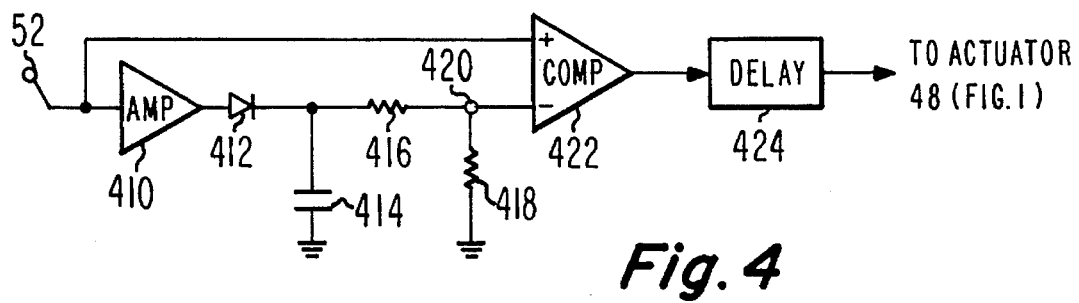
FIG. 4 is a simplified diagram of a circuit for identifying a portion of the voltages corresponding to a particular portion of the hearts' cycle.

While there are many ways to process waveforms to identify a particular portion thereof, one very simple way is to detect or "DC restore" the waveform, and then identify the time at which the waveform crosses a particular threshold. FIG. 4 is a simplified representation of a processing circuit which may be used in controller block 50 of FIG. 1. In FIG. 4, an electrode 52 produces a waveform such as 310 of FIG. 3 relative to a reference potential illustrated by a ground symbol, and applies it to the input port of a follower amplifier 410 for isolation and impedance transformation. The transformed signal is applied to a detector including a rectifier diode 412 and a current integrating capacitor 414. A voltage is generated across capacitor 414 which represents the historic peak-to-peak magnitude of the incoming waveform. A pair of series-connected resistors 416, 418 connected across capacitor 414 cause a discharge which results in a diminution with time of the voltage across the capacitor, which voltage is restored by the most recent waveform portion. This has the effect of making the voltage across capacitor 414 representative of the peak-to-peak magnitude of the latest, or a few of the latest, of the waveforms, rather than the historic maximum value. Resistor pair 416, 418 together constitute a voltage divider having a tap 420. The relative magnitudes of the resistors may be selected to produce any proportion of the peak-to-peak representative signal at tap 420. The resistor values may be selected to give, for example, a 95% proportion. The input signal waveform may be expected to equal the 95% value at the tap of the voltage divider twice during each heart beat or cycle, for example at times Ta and Tb of FIG. 3. Thus, a comparator 422, having its noninverting input port connected to electrode 52 and its inverting input port connected to tap 420, will produce a positive-going pulse during each interval Ta to Tb, and a negative-going signal portion in the following interval Tb-Ta. The pulse produced by comparator produces a basic time reference related to the operation of the heart.

Once a basic time reference related to the operation of the heart of the patient has been established by the arrangement of FIG. 4 as so far described, a simple delay is sufficient to "mark" or identify any other portion of the heart cycle. For example, a simple delay of one-half of a heart cycle duration from time Ta identifies a time just before time T3 of FIG. 3. A delay circuit illustrated as 424 in FIG. 4 responds to the pulse produced by comparator 422, and produces a delayed pulse. One convenient form of delay element is a multivibrator (MVB). The output of the multivibrator (MVB) is applied to control actuator 48 of FIG. 1, to drive it alternately to the right during one portion of the multivibrator cycle and to the left during the other portion. The multivibrator preferably produces a square wave, which is a voltage or current wave having equal duration "high" and "low" time portions, so that the actuator dwells for equal times at the inflation and deflation positions of valve 42.

As so far described, the system inflates and deflates the angioplasty balloon during each heart cycle. It may be found to be convenient to synchronize to every other heart cycle, or every third or fourth, etc. Thus, the balloon might remain inflated for two cycles, followed by two cycles of deflation. Even further, there is no particular requirement that the number of heart cycles during which the balloon is inflated equal the number of cycles during which it is deflated. The number of "skipped" heart cycles may be selected simply by increasing the delay imparted by the multivibrator to include the duration of one or more integer heart cycle intervals, so that the inflation pressure is controlled for tending to inflate the balloon with fluid during certain ones of the systolic portions of the heartbeat, and for tending to deflate the balloon during diastolic portions of the heartbeat which follow the next systolic portion subsequent to the certain one of the systolic portions.

Figure 5:
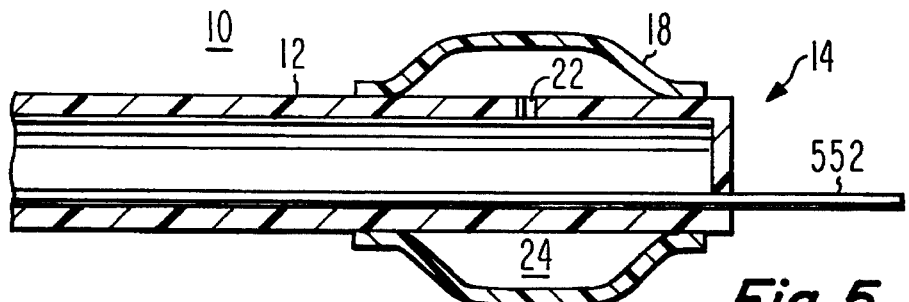
FIG. 5 is a simplified representation of the distal end of a catheter according to another embodiment of the invention.

FIG. 5 is a simplified representation of the distal end of a catheter according to another embodiment of the invention. Elements of FIG. 5 corresponding to those of FIG. 1 are designated by like reference numerals. In FIG. 5, an electrically conductive wire electrode 552 extends through the length of catheter 10, and protrudes beyond distal end 14 of catheter body 12. The protruding portion may be formed or shaped in a manner selected to make contact with the adjacent walls of a blood vessel, for sensing heart voltages appearing at that location, or it may simply lie in the blood stream, in which case it will still sense heart voltages. This arrangement may be desirable as a substitute for one of the external electrodes for sensing the heart voltages or potentials, because it is closer to the location of the balloon than an externally placed electrode, and may provide a more definite indication of the state of the hearts' cycle.

Figure 6:
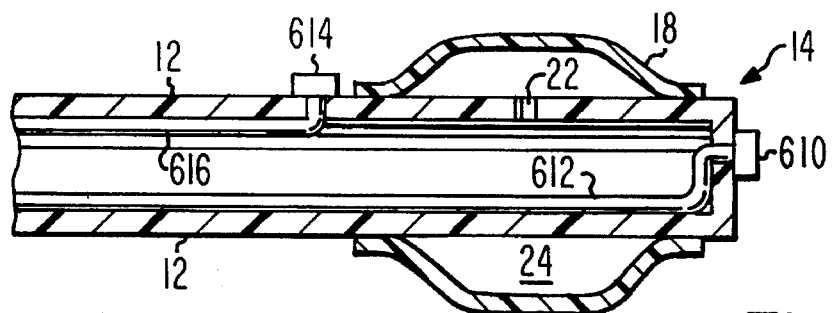
FIG. 6 is a simplified representation of the distal end of a catheter according to another embodiment of the invention.

FIG. 6 is a simplified representation of the distal end of a catheter according to another embodiment of the invention. Elements of FIG. 6 corresponding to those of FIG. 1 are designated by like reference numerals. In FIG. 6, a blood pressure sensor 610 is coupled to an outer surface of the distal end of the catheter, and is connected by a pressure tube (for a mechanical sensor) or by an electrical wire 612 (for an electrical sensor) to the proximal end (not illustrated), where it may be coupled to a controller much as described above. The pressure sensor may alternatively, or additionally, be connected on the other side of the balloon, as illustrated by sensor 614 and its connecting path 616.

Other embodiments of the invention will be apparent to those skilled in the art. While the described apparatus includes a catheter with a single lumen, other lumens may be provided for various purposes, and other facilities may be provided in conjunction with the balloon, such as a fiber optic scope with single or multiple fibers for viewing or for laser surgery, electrical wires for electroerosion, for sensing or for other purposes, transmission lines for microwave heating or sensing, mechanical implements for cutting, abrading or the like, guide wires or filaments, and any other facilities which normally accompany catheters. Any arrangement for changing the pressure in the inflation lumen may be used, as for example a rapid-acting pump for directly producing the desired alternating pressures, instead of the two separate reservoirs as described.

What is claimed is:

1. A method for performing balloon angioplasty on a patient, inserting into a coronary artery of said patient a balloon catheter including a balloon inflation orifice at a proximal end thereof; and generating and coupling to said balloon catheter balloon inflation and deflation pressures, which cycle in an automatic manner between said inflation and deflation pressures in such a manner as to inflate said balloon during systole, and deflate said balloon during diastole.

2. A method according to claim 1, wherein said step of generating and coupling comprises the further steps of:

generating signals representative of the recurrent cycle of operation of the heart of said patient; and controlling said cycling of said inflation and deflation pressures in response to said signals.

3. A method according to claim 2, wherein said step of controlling said cycling includes the recurrent steps of:

coupling said inflation pressure to said balloon catheter during those times in which said signals indicate that systolic portions of said heartbeat are occurring; and coupling said deflation pressure to said balloon catheter during those times in which said signals indicate that diastolic portions of said heartbeat are occurring.

* * * * *